United States Patent [19]

Keyvani et al.

[11] Patent Number: 5,693,862
[45] Date of Patent: Dec. 2, 1997

[54] PROCESS FOR TRANSPORT OF TOLUENEDIAMINE

[75] Inventors: Majid Keyvani; Rekha Menon; James L. Meyer; Thomas W. Offill, all of Lake Charles, La.

[73] Assignee: Arco Chemical Technology, L.P., Greenville, Del.

[21] Appl. No.: 769,255

[22] Filed: Dec. 18, 1996

[51] Int. Cl.$^6$ .................................................. C07C 209/90
[52] U.S. Cl. ......................... 564/305; 564/5; 564/420; 564/421; 564/422; 564/423
[58] Field of Search .......................... 564/5, 305, 420, 564/421, 422, 423

[56] References Cited

U.S. PATENT DOCUMENTS 5,449,832  9/1995  Carr et al. ............................ 564/305

Primary Examiner—Richard L. Raymond
Attorney, Agent, or Firm—Dale Lynn Carlson; Todd E. Garabedian; Wiggin & Dana

[57] ABSTRACT

The present invention is directed to a process for transporting toluenediamine (TDA) from a first site to a second site. The process of the invention comprises the steps of (a) providing a molten mass of TDA isomers at the first site; (b) cooling the molten mass to a temperature below the melting point, the molten mass thereby forming flowable particles of solid TDA in an inert gas; (c) providing an airtight storage vessel lined with a chemically inert liner; (d) storing the flowable particles of solid TDA in the lined storage vessel; (e) charging the storage vessel with inert gas; (f) transporting the storage vessel from the first site to the second site; and (g) remelting the TDA flowable particles in inert gas with TDA liquid that is superheated above the melting point to produce a molten TDA isomer mixture in inert gas having substantially the same isomer ratio as that of the molten mass. Also disclosed is a process for storing TDA in a cost-effective manner while reducing the likelihood of TDA degradation during storage, relative to conventional TDA storage methods.

15 Claims, No Drawings

PROCESS FOR TRANSPORT OF TOLUENEDIAMINE

FIELD OF THE INVENTION

This invention relates generally to a method for storing toluenediamine (TDA), and more particularly to a method for storing the TDA in solid form in a manner that minimizes or reduces the risk of degradation that might otherwise occur. The method is particularly useful for transporting TDA from one site to another, e.g., by ship, truck, or rail car.

BACKGROUND OF THE INVENTION

Toluene diisocyanate (TDI) is a commodity chemical intermediate used worldwide as one of the major raw materials for manufacturing flexible polyurethane foams. The production of TDI from primary raw materials, such as natural gas and petrachemicals, typically requires the use of chemical intermediates from more than one chemical plant using diverse chemical process technologies.

By way of illustration, one preferred commercial reaction pathway utilities natural gas to produce ammonia, followed by the oxidation of ammonia to nitric acid, reaction of nitric acid with toluene to produce dinitrotoluene (DNT) isomers, including the meta isomers, hydrogenation of DNT isomers to produce toluenediamine (TDA) isomers including meta TDA, and isolation of the meta TDA isomers, which are then phosgenated to produce TDI. Of course, this supply chain uses hydrogen and phosgene produced from another supply chain, preferably involving the reforming of natural gas to hydrogen and carbon monoxide, and the reaction of the carbon monoxide with chlorine to produce phosgene.

A high volume TDI plant requires that each of these intermediates be produced in significant quantities from chemical processes requiring a multitude of unit operations and discrete pieces of equipment, resulting in a significant capital investment. Accordingly, the manufacture of the desired TDI product requires the construction of major chemical complexes adjoining the TDI plant or within a short distance (local) to the TDI plant such that the cost of transport of the multitude of raw materials is not cost prohibitive. In view of the complexity and capital investment needs of this type of business endeavor, only a limited number of large-scale, fully integrated TDI plants with favorable, low-cost economies of scale exist today.

From the perspectives of product marketing and customer supply, it is highly desirable to produce TDI in local markets, close to where it is consumed. Transport of TDI for only short distances is safer, reducing the risk of spillage or other releases of TDI to the environment during the transportation of this hazardous chemical. In addition, the production of TDI in local markets can avoid import restrictions from local governments, thus eliminating or reducing several operating cost elements, such as tariffs, duties, shipping and handling fees. These needs have previously been recognized and small, local TDI manufacturing complexes have been constructed with full integration of precursor raw materials, but the resulting high manufacturing costs due to disadvantageous small-scale economies have generally resulted in uncompetitive production costs for these small plants, as compared to TDI made in a large scale foreign plant and then imported.

As a result of this economic situation, much TDI is transported from large-scale TDI complexes to distant markets where it is consumed in production of polyurethane foam for local markets. Furthermore, the current situation is exacerbated by the fact that in the recent past and the foreseeable future, the growth of TDI demand is highest in remote regions of the world where the base demand is insufficient to justify the construction of large-scale TDI manufacturing complexes with fully integrated manufacture of raw material intermediates. Hence, there is a growing, unsatisfied demand for small-scale TDI manufacturing facilities that would have reduced capital cost intensity and, therefore, more competitive overall costs.

Many of the disadvantages associated with TDI manufactured in these smaller, remote plants that are sized to meet local demand could be overcome if TDA, the key intermediate raw material, could be safely and cost-effectively shipped, with minimal chemical degradation, from a large-scale TDA plant to the small, remote TDI plant. This approach would provide the economies experienced in large-scale, back-integrated TDA plants with the lower capital cost intensity required to make local TDI plants competitive.

Heretofore, various efforts have been made to provide technology for shipping TDA to local TDI plant sites. Unfortunately, this can be difficult. TDA is an aromatic diamine with a high melting point of about 210°–220° F., depending on the isomer composition. Toluenediamine (TDA), which is suitable for the production of commercial grades of TDI, contains mostly meta isomers (65–85% 2,4- and 15–35% 2,6-), but also can contain minor amounts of para isomers (0–1% 2,5 and 0–1% 3,5) and ortho isomers (0–3% 2,3- and 0–3% 3,4-). Because of its high melting point, storage and transport of TDA is difficult. A number of processes have been developed in an effort to store and transport TDA.

One approach utilized heretofore in the U.S. involves the storage and transport of the toluenediamine isomer mixture as a molten liquid, typically in small vessels, trucks, or railcars that are equipped to maintain the toluenediamine at an elevated temperature in excess of its melting point. These methods are suitable for use in local markets. However, long-term storage and transport as a liquid in large containers, such as present in ocean-going vessels, is extremely difficult for several reasons. First, there is a lack of equipment suitable for maintaining the stored material above the melting point. Second, there is an operational energy cost associated with maintaining the temperature above the TDA melting point for extended periods of time. Third, there is an increased level of chemical degradation of TDA to unusable tars when the material is maintained at high temperature for extended periods of time.

A second approach, as illustrated by the disclosures of U.S. Pat. No. 5,449,832 assigned to Air Products and Chemicals, Inc., involves methodology for preparing meta-toluenediamine for storage and transport of TDA under liquid phase conditions with reduced freezing point by adding water in an amount of from 5–15% by weight of molten TDA. This method is an improvement over the previously discussed approach, but still suffers significant drawbacks, including: (1) the shipping vessel still requires equipment and energy to maintain the mixture temperature above 150° F.; (2) contamination of the ship with a hazardous chemical requires dedicated ship/container at high cost. Significant costs are also incurred when a ship returns empty, or must be decontaminated; (3) addition of water to TDA results in higher weight and therefore higher freight costs; and (4) after unloading the TDA-water mixture, it is necessary to remove the water from the TDA before converting it to TDI, thereby generating TDA-contaminated waste water.

A third approach utilized heretofore involves allowing a portions or all of a drum-quantity shipment of molten TDA to solidify into large blocks as temperature is reduced below the melting point. The blocks are then suitably stored and shipped using conventional, non-heated transportation equipment. However, remelting of solid TDA is problematic due to poor heat transfer. During the long time required to completely melt the solid, the toluenediamine will undergo chemical degradation. Furthermore, the significant handling required to produce, transport, and remelt large quantities of solid TDA potentially subjects personnel involved in handling, shipping and operations to hazardous industrial hygiene conditions, particularly in view of the fact that, based on animal feeding studies, the U.S. Environmental Protection Agency (EPA) has determined TDA to be a suspect carcinogen. In order to handle large amounts of solid TDA, elaborate engineering controls and personal protective equipment would be needed to minimize worker exposure to TDA.

Thus, there is a need in the art for a method of storing and/or transporting TDA in a safe, economical manner that minimizes breakdown of the TDA being stored and/or transported. The present invention is believed to be an answer to that need.

SUMMARY OF THE INVENTION

In one aspect, the present invention relates to a process for transporting toluene diamine from a first site to a second site, comprising the steps of:

(a) providing a molten mass of TDA isomers at said first site;

(b) cooling said molten mass to a temperature below the melting point of said TDA isomers, and converting said molten mass into flowable particles of solid TDA in an inert gas;

(c) providing an airtight storage vessel lined with a vessel liner that is chemically inert to said flowable particles of solid TDA;

(d) filling at least a portion of said lined storage vessel with said flowable particles of solid TDA;

(e) charging said storage vessel with an inert gas;

(f) transporting said storage vessel from said first site to said second site; and (g) melting said flowable particles by contacting said flowable particles with liquid TDA that is superheated above the melting point to produce a molten TDA isomer mixture having substantially the same isomer ratio as said molten mass.

In another aspect, the present invention relates to a degradation-free process for storing TDA which comprises the steps of:

(a) providing a molten mass having a predetermined isomer ratio of TDA isomers;

(b) cooling said molten mass to a temperature below the melting point of said TDA isomers, and converting said molten mass into flowable particles of solid TDA in an inert gas;

(c) providing an airtight storage vessel lined with a vessel liner that is chemically inert to said flowable particles of solid TDA;

(d) filling at least a portion of said lined storage vessel with said flowable particles of solid TDA;

(e) charging said storage vessel with inert gas, and;

(f) melting said flowable particles by contacting said flowable particles with liquid TDA that is superheated above the melting point to produce a molten TDA isomer mixture in said inert gas, said isomer mixture having an isomer ratio of TDA isomers that is substantially identical to said predetermined isomer ratio of said molten mass.

In yet another aspect, the present invention relates to a process for transporting toluene diamine from a first site to a second site, comprising the steps of:

(a) controllably cooling a molten mass of TDA isomers at said first site in order to convert said molten mass into flowable particles of said TDA, and maintaining said flowable particles in a blanket of an inert gas;

(b) transporting said flowable particles in said blanket of said inert gas from said first site to said second site; and, (c) melting said flowable particles by contacting said flowable particles with liquid TDA that is superheated above the melting point to produce a molten TDA isomer mixture having substantially the same isomer ratio as the molten TDA isomers of step (a).

These and other aspects will become apparent upon reading the following detailed description of the invention.

DETAILED DESCRIPTION OF THE PREFERRED EMBODIMENTS

The present invention is directed to an economical method of transporting toluenediamine (TDA) that includes 1) converting molten liquid to solid flowable particles, 2) loading and transporting the TDA flowable particles in standard overseas shipping containers fitted with a disposable plastic liner, and 3) unloading the material at the off-shore plant and remelting the flowable particles for direct feeding to the TDI plant. It has now been surprisingly found that the process of the present invention is suitably employed to store and/or transport TDA without significant chemical or physical degradation of the TDA. Advantageously, in accordance with the present invention, the TDA maintains flowability throughout the required processing, shipping, and/or handling to which the TDA is subjected.

Toluenediamine is produced and consumed as a liquid isomer mixture having a melting point of about 210° F. Toluenediamines (TDA) are typically manufactured by hydrogenation of dinitrotoluene, which is produced by the nitration of toluene. It has been observed that TDA can be degraded to form polymeric compounds (tars), ammonia, and water. The tars that are formed from TDA degradation do not produce TDI when reacted with phosgene and therefore result in yield losses to the TDI manufacturing process. Furthermore, tars contained in the TDA feed to a TDI plant can lead to surface coating of heat transfer surfaces and equipment pluggage, necessitating periodic production interruptions to clean the equipment. Hence, it is highly desirable to minimize the formation of tars in the production and handling of TDA.

Due to the ability of the nitrating agent to attack multiple locations on the toluene aromatic ring, TDA is produced as a mixture of isomers. TDA, which can be used for the production of commercial grades of TDI, contains mostly meta isomers (65–85% 2,4- and 15–35% 2,6-), but also can contain minor amounts of para isomers (0–1% 2,5 and 0–1% 3,5) and ortho isomers (0–3% 2,3- and 0–3% 3,4-). The meta TDA isomers are present in the largest quantities and can be readily reacted with phosgene to produce commercial TDI in high yield using previously disclosed commercial processes. Likewise the para isomers, typically present as about 0–7% 2,5 TDA and <0.1% 3,5 TDA, can be readily converted through phosgenation to the corresponding toluene diisocyanate isomers. It has also been previously disclosed that the ortho-TDA isomers (3,4 and 2,5 TDA) are not readily converted to the corresponding isocyanates and result in by-products formation and yield losses in phosgenation processes.

Despite the almost identical molecular structure, it has been discovered that TDA isomers degrade at different rates when subjected to heat or exposed to the oxygen in air or water. From the data in Table 1, it can be seen that the meta-TDA isomers present in the largest quantities (2,4 and 2,6 TDA) have the lowest degradation results. It was also found that the ortho-TDA isomers (3,4 and 2,5 TDA) have relatively high degradation rates. Since they are not readily converted to the corresponding isocyanates when phosgenated, these isomers are often separated from the other isomers prior to phosgenation using known processes, including removal in a low boiling portion through fractional distillation. However, it was found that the para-TDA isomer (2,5 TDA), which can be readily converted to TDI, also exhibits high degradation rates when exposed to heat and/or air. Moreover, the para-TDA isomer has a boiling point intermediate between the ortho-TDA and meta-TDA isomers, and is very difficult to remove without incurring losses of meta-TDA through incomplete separations. Hence it is highly desirable to leave the para-TDA isomer in the meta-TDA feed stream to the TDI plant, provided the degradation rate to tars is not high.

TABLE 1

| | Tars formed when the isomers were kept at 250° F. for 2 hrs | |
|---|---|---|
| Isomer | Tars formed under N$_2$ (%) | Tar - under air (%) |
| 2,4 TDA | 0.02 | 0.32 |
| 2,6 TDA | 0.11 | 0.31 |
| 3,4 TDA | <0.01 | 1.90 |
| 2,3 TDA | 0.31 | 0.76 |
| 2,5 TDA | 0.23 | 0.71 |

TDA was found to be attacked by oxygen in air when a blanket of air was used, to form water, ammonia and polymeric compounds (i.e., tars). These tars, formed by oxidative polymerization, have been found in accordance with the present invention to act like binders, tending to cause the solid particles of TDA to form agglomerates. Hence, tar formation must be minimized in order to avoid this agglomeration phenomenon.

The steps of solidifying, transporting and remelting the TDA in accordance with the present invention is illustrated as follows:

Step (I)—Solidifying molten TDA:

The process of solidification involves cooling molten TDA by direct or indirect heat exchange and then solidifying it below the melting point. Some methods of solidification of molten TDA include, but are not limited to, flaking, prilling, pelletizing, freeze crystallization, and the like. A key criterion for selection of the method of solidification employed is the level of flowability desired, since highly flowable material is less subject to physical degradation, and has a low tendency to agglomerate in inert environments. Some of the equipment available for the solidification of molten TDA include the flaker, priller, pelletizer, as well as other know solidification apparatus. The preferred equipment in this process is the flaker.

Illustratively, flakers of conventional design are suitably used to produce flowable particles of TDA in the form of flakes. For example, molten TDA at about 225° F. is suitably fed from a storage tank to a pan and picked up as a film on a partly immersed, rotating drum. Coolant is contacted with the internal surface of the drum, thereby reducing the external surface temperature of the drum to a temperature of from about −40° F. to about 180° F., preferably from 30° F. to 120° F., thereby cooling the TDA to below its melting point and freezing the TDA. The TDA is subsequently removed from the drum by a knife to form solid, flowable particles. The size of the required flaker is reduced by using chilled water as the cooling media to provide an advantageous exposure of the molten TDA to the temperature differential between it and the chilled drum surface.

When exposed to air, the TDA flowable particles can absorb moisture and be degraded by oxygen, producing tars. Tars would constitute a yield loss and typically leads to material agglomeration in a container. To avoid these problems, the TDA flowable particles must be produced and transported in an inert (preferably a dry nitrogen) atmosphere. Criteria for producing the desired solidification include control the cooling residence time and the rate of cooling in order to optimize the desired production of discrete particles, rather than a mass of particles. The temperature of the molten mass must be kept high enough to maintain it in a molten state prior to the desired controlled solidification, but low enough to avoid degradation of the TDA. In addition, the molten mass must be kept under a blanket of inert gas (such as nitrogen, argon, helium, hydrogen, or combinations thereof) in order to avoid the degradation that otherwise results from exposure of TDA to the oxygen in atmospheric air or water.

Step (II)—Transporting solid TDA

As the TDA flowable particles are produced, they are collected in a hopper and subsequently transferred to standard shipping containers. A totally enclosed, dust-tight container design is required due to the susceptibility of air oxidation and the toxic nature of the material. Inert gas(es) must be used in order to protect the TDA particles from the oxygen in air or atmospheric moisture. Any gas that is inert to the TDA being transported is suitably employed as the inert gas (e.g., argon, nitrogen, helium, hydrogen, and combinations thereof). Nitrogen is generally preferred because of its low cost and easy availability.

The TDA flowable particles are physically and chemically degradable, and hence the method used to transport this material must be suitably selected to avoid applying undue force or exposure to the TDA being transported. The criteria in the selection of the transport equipment include the need to minimize chemical and physical degradation, and the need to avoid exposure to oxygen by employing an inert environment, such as a nitrogen blanket. A preferred transport method is dense phase pneumatic conveying which can efficiently transport TDA flowable particles to product containers with minimum chemical and physical degradation. This technology typically uses a small amount of an inert gas, such as nitrogen, to facilitate moving bulk solid material in closely associated slugs through the conveying line.

Typical bulk shipping containers used in the process of the invention include lined containers that are about 20 to 40 feet long, eight feet high, and eight feet wide. Typical liners for the container can be made of polyethylene with or without woven polypropylene for reinforcement. The liners are preferably completely sealed to protect the product, impermeable to air, easily removable and disposable, thereby avoiding direct contact between the TDA solid material and the container. Using liners, product loss from contamination and breakage is drastically reduced along with a reduction in the amount of product released into the atmosphere during loading and handling.

The flaker and loading system design should preferably totally contain the TDA to comply with environmental regulations and industrial hygiene requirements. If desired, provisions for environmental controls may be included to manage any unusual dust and spills without triggering reportable quantity incidents (i.e., an escape of greater than ten pounds of TDA to environment).

Step (III)—Melting solid TDA at the remote TDI plant

The melting of the TDA solids at the remote TDI plant is preferably accomplished by a continuous process where the solid is fed and dispersed into molten TDA under an inert (preferably nitrogen) atmosphere. Suitable equipment includes various trough or cylindrical agitated heat transfer devices with solids feed on one end and molten TDA liquid leaving the other, or conventional, heated and agitated tanks with solids feed to the top.

Preferably, the solid flowable particles are exposed to the molten TDA for a short time, preferably between 12 to 30 minutes, in order to minimize extended heating time and subsequent tars formation. In addition, the temperature of the heating media and the TDA solid/liquid slurry should be maintained at the lowest practical level to minimize TDA degradation within the melting equipment. Although a wide range of temperatures is suitably employed, the range is advantageously between 215° F. and 350° F., more preferably between 225° F. and 300° F. Once again, an inert gas environment should be employed above the level of the TDA solid/liquid slurry in the equipment selected in order to minimize the formation of tars. Thus, the criteria for selection of the melting method include the need for a low residence time and a moderate temperature in the melter apparatus in order to facilitate throughput and minimize the risk of TDA degradation. Meeting these criteria is advantageously facilitated using both direct and indirect heating of the particulate TDA using a molten TDA bath.

The melting equipment should be designed to maximize the productivity for melting TDA flowable particles without carrying forward TDA solids downstream, which could plug the lines and pumps. Meeting the criterion of minimizing TDA degradation facilitates keeping the melting equipment clean, since the risk of equipment fouling is also minimized.

The melted TDA is suitably employed to produce TDI for use as an intermediate in the production of polyurethane foam, as described in the Background of the Invention hereinabove.

The transport method of the invention provides numerous advantages over transport methods known in the prior art. In particular, the method of the invention utilizes standard, readily available shipping containers, which can be flexibly and safely moved to remote locations without extraordinary equipment. In addition, the method of the invention minimizes shipping weight by avoiding the use of solvents, yet does not require auxiliary equipment and energy costs to heat the shipping vessel beyond the ambient air temperature. The method of the invention further eliminates direct contact of toluenediamine with the shipping container, thereby minimizing decontamination requirements and avoiding the generation of contaminated waste water.

The method of the invention provides the further advantage in that the method does not require the use of a solvent (i.e. water) to reduce the melting point of a TDA mixture. Thus, the need for processing equipment to add and subsequently remove the solvent is eliminated, as well as costs and waste generation that would have resulted from these processing steps. The method of the invention also achieves high transfer rate in melting the TDA solids by dispersing the solids in heated, molten TDA, thereby avoiding the poor heat transfer rate normally associated with heating solids directly through a heat transfer surface with poor contact. The method of the invention further allows all TDA handling steps to be designed and continuously operated with fully contained equipment thereby reducing risk of worker exposure to TDA, which is hazardous to handle directly.

The method of the invention provides the further advantages in that the method avoids high temperature exposure of toluenediamine for extended time, thus reducing product degradation and yield losses. The method of the invention further prevents exposure of TDA to ambient air during transport by containment of TDA particles within a flexible, impermeable container liner, thereby protecting the quality of TDA and minimizing subsequent yield losses in the conversion of the material to TDI. The method of the invention further allows virtually complete recovery of the shipped TDA from the disposable container liner, minimizing chemical losses and waste generation.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications are incorporated by reference in their entirety.

What is claimed is:

1. A process for transporting toluene diamine from a first site to a second site, comprising the steps of:
   (a) providing a molten mass of TDA isomers at said first site;
   (b) cooling said molten mass to a temperature below the melting point of said TDA isomers, and converting said molten mass into flowable particles of solid TDA in an inert gas;
   (c) providing an airtight storage vessel lined with a vessel liner that is chemically inert to said flowable particles of solid TDA;
   (d) filling at least a portion of said lined storage vessel with said flowable particles of solid TDA;
   (e) charging said storage vessel with an inert gas;
   (f) transporting said storage vessel from said first site to said second site; and
   (g) melting said flowable particles by contacting said flowable particles with liquid TDA that is superheated above the melting point to produce a molten TDA isomer mixture having substantially the same isomer ratio as said molten mass.

2. The process of claim 1 wherein said inert gas is selected from the group consisting of nitrogen, argon, helium, hydrogen and combinations thereof.

3. The process of claim 1 wherein said cooling is effected at a temperature of from about −40° F. to about 180° F.

4. The process of claim 1 wherein said melting is effected at a temperature of from about 215° F. to about 350° F.

5. The process of claim 1 wherein said melting is effected at a temperature of from about 225° F. to about 300° F.

6. A degradation-free process for storing TDA which comprises the steps of:
   (a) providing a molten mass having a predetermined isomer ratio of TDA isomers;
   (b) cooling said molten mass to a temperature below the melting point of said TDA isomers, and converting said molten mass into flowable particles of solid TDA in an inert gas;

(c) providing an airtight storage vessel lined with a vessel liner that is chemically inert to said flowable particles of solid TDA;

(d) filling at least a portion of said lined storage vessel with said flowable particles of solid TDA;

(e) charging said storage vessel with inert gas, and;

(f) melting said flowable particles by contacting said flowable particles with liquid TDA that is superheated above the melting point to produce a molten TDA isomer mixture in said inert gas, said isomer mixture having an isomer ratio of TDA isomers that is substantially identical to said predetermined isomer ratio of said molten mass.

7. The process of claim 6 wherein said inert gas is selected from the group consisting of nitrogen, argon, helium, hydrogen and combinations thereof.

8. The process of claim 6 wherein said cooling is effected at a temperature of from about −40° F. to about 180° F.

9. The process of claim 6 wherein said melting is effected at a temperature of from about 215° F. to about 350° F.

10. The process of claim 6 wherein said melting is effected at a temperature of from about 225° F. to about 300° F.

11. A process for transporting toluene diamine from a first site to a second site, comprising the steps of:

(a) controllably cooling a molten mass of TDA isomers at said first site in order to convert said molten mass into flowable particles of said TDA, and maintaining said flowable particles in a blanket of an inert gas;

(b) transporting said flowable particles in said blanket of said inert gas from said first site to said second site; and, (c) melting said flowable particles by contacting said flowable particles with liquid TDA that is superheated above the melting point to produce a molten TDA isomer mixture having substantially the same isomer ratio as the molten TDA isomers of step (a).

12. The process of claim 11 wherein said inert gas is selected from the group consisting of nitrogen, argon, helium, hydrogen and combinations thereof.

13. The process of claim 11 wherein said cooling is effected at a temperature of from about −40° F. to about 180° F.

14. The process of claim 11 wherein said melting is effected at a temperature of from about 215° F. to about 350° F.

15. The process of claim 11 wherein said melting is effected at a temperature of from about 225° F. to about 300° F.

\* \* \* \* \*